United States Patent
Roberts et al.

(10) Patent No.: US 6,733,754 B2
(45) Date of Patent: May 11, 2004

(54) ADJUVANTS FOR USE IN VACCINES

(75) Inventors: David S. Roberts, Philadelphia, PA (US); Leroy A. Swearingin, Waterford, CT (US); Don A. Dearwester, Westerly, RI (US)

(73) Assignees: Pfizer, Inc., New York, NY (US); Pfizer Products, Inc., Croton, CT (US)

( * ) Notice: Subject to any disclaimer, the term of this patent is extended or adjusted under 35 U.S.C. 154(b) by 0 days.

(21) Appl. No.: 10/389,139

(22) Filed: Mar. 13, 2003

(65) Prior Publication Data

US 2003/0175299 A1 Sep. 18, 2003

Related U.S. Application Data

(62) Division of application No. 09/489,713, filed on Jan. 24, 2000, now Pat. No. 6,572,861
(60) Provisional application No. 60/117,705, filed on Jan. 29, 1999, now abandoned, and provisional application No. 60/121,760, filed on Feb. 26, 1999, now abandoned.

(51) Int. Cl.$^7$ ............................................. A61K 39/00
(52) U.S. Cl. .................. 424/184.1; 424/203.1; 424/209.1; 424/234.1; 424/254.1; 424/255.1; 424/256.1; 424/263.1; 424/283.1; 424/438; 424/278.1; 424/458; 424/460; 424/490; 424/492; 424/682; 424/825; 424/94.1; 554/80
(58) Field of Search ...................... 424/203.1, 184.1, 424/209.1, 210.1, 234.1, 254.1, 255.1, 256.1, 263.1, 278.1, 283.1, 438, 458, 460, 264.1, 253.1, 825, 236.1, 93.3

(56) References Cited

U.S. PATENT DOCUMENTS

| | | | | |
|---|---|---|---|---|
| 4,789,544 A | * | 12/1988 | Nelson et al. | 424/92 |
| 5,338,543 A | * | 8/1994 | Fitzgerald et al. | 424/264.1 |
| 5,612,042 A | * | 3/1997 | Jacobs | 424/237.1 |
| 5,665,363 A | * | 9/1997 | Hansen et al. | 424/211.1 |
| 5,695,769 A | * | 12/1997 | Frantz et al. | 424/255.1 |
| 5,888,513 A | * | 3/1999 | Plana Duran et al. | 424/186.1 |
| 5,968,525 A | * | 10/1999 | Fitzgerald et al. | 424/264.1 |
| 6,013,266 A | * | 1/2000 | Segers et al. | 424/234.1 |
| 6,517,843 B1 | * | 2/2003 | Ellis et al. | 424/204.1 |
| 6,572,861 B1 | * | 6/2003 | Roberts et al. | 424/203.1 |

FOREIGN PATENT DOCUMENTS

| | | | | |
|---|---|---|---|---|
| DE | 2816942 | * | 11/1978 | C12K/5/00 |
| DE | 3517805 | * | 11/1986 | C12N/1/20 |
| EP | 597852 | * | 12/1997 | A61K/39/02 |
| EP | 651609 | * | 11/1999 | C07K/14/285 |

* cited by examiner

Primary Examiner—Lynette R. F. Smith
Assistant Examiner—Ginny Allen Portner
(74) Attorney, Agent, or Firm—Paul H. Ginsburg; Lorraine B. Ling; Kohn & Associates, PLLC

(57) ABSTRACT

The invention relates to adjuvants that contain a lecithin, an oil and an amphiphilic surfactant and that are capable of forming a stable oil-in-water emulsion vaccine so as to minimize local reactions to the vaccine in the injected animal.

1 Claim, 1 Drawing Sheet

ADJUVANTS FOR USE IN VACCINES

Figure 1:
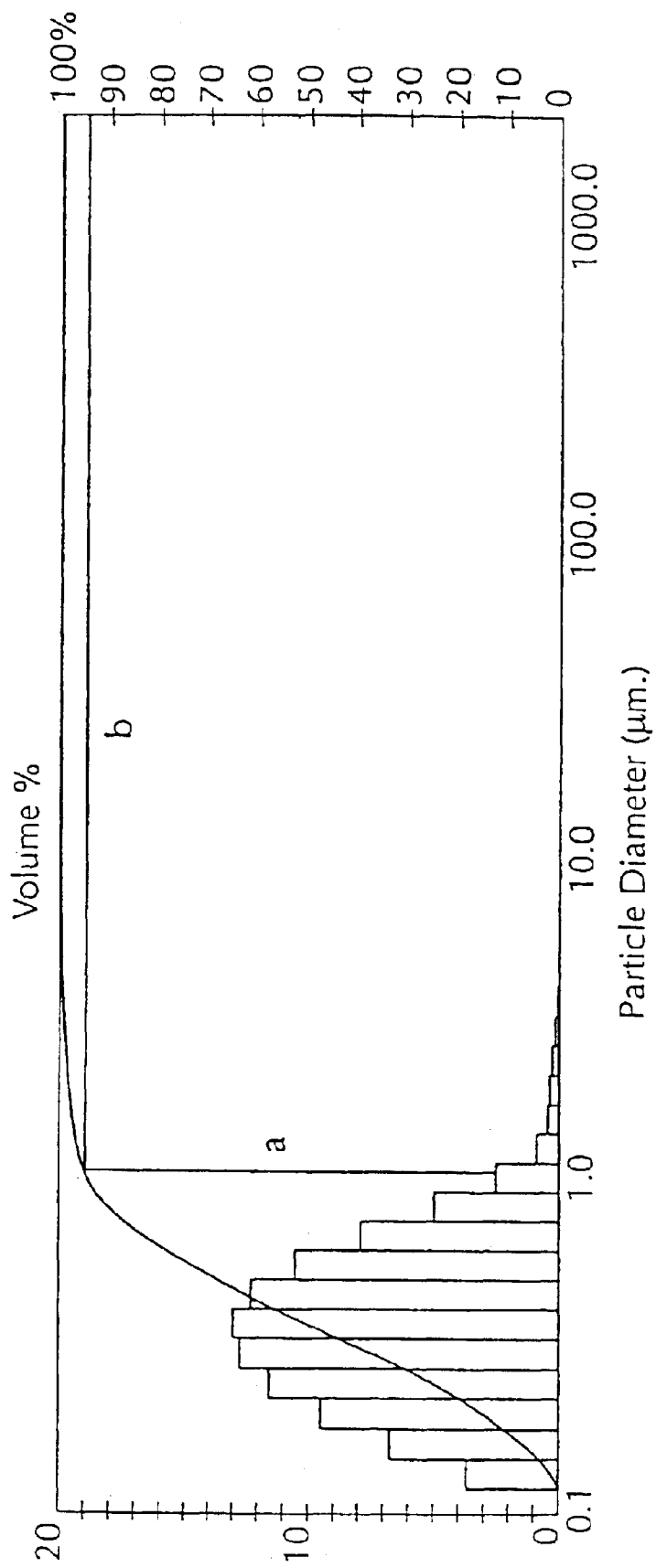

This application is a divisional application of U.S. patent application Ser. No. 09/489,713, filed Jan. 24, 2000 now U.S. Pat. No. 6,572,861, which claims the benefit of priority to U.S. Provisional Application No. 60/117,705, filed Jan. 29, 1999 now abandoned, and U.S. Provisional Application No. 60/121,760, filed Feb. 26, 1999 now abandoned, all of which are incorporated herein by reference.

FIELD OF THE INVENTION

The invention relates to immunological adjuvants. In particular, the invention relates to adjuvants which comprise an oil-in-water emulsion and a surfactant. Adjuvants of the invention are useful in a variety of vaccine formulations, including vaccines comprising bacterial or viral components.

BACKGROUND OF THE INVENTION

The generation of immunity to infectious organisms is a powerful tool in disease control. Those antigens that induce immunity to infection are known as immunogens. The protective antibody they induce may collaborate with other natural defenses to inhibit the infective process, or they may neutralize harmful products of the infective organism such as toxins.

An effective means of enhancing the antibody response is the use of an adjuvant. Thus, an adjuvant is included in a vaccine as an additive or vehicle to enhance the response to the antigen. An adjuvant may function by different mechanisms, including (1) trapping the antigen in the body to cause a slow release, (2) attracting cells of the immune system to the injection site, (3) stimulating cells of the immune system to proliferate and to become activated, and (4) improving antigen dispersion in the recipient's body.

A number of agents with diverse chemical properties have been used as adjuvants, including water-in-oil and oil-in-water emulsions, mineral salts, polynucleotides and natural substances. One adjuvant, known under the trademark AMPHIGEN™, is described in U.S. Pat. No. 5,084,269. AMPHIGEN™ adjuvant consists of de-oiled lecithin dissolved in an oil, usually light liquid paraffin. In vaccine preparations AMPHIGEN™ is dispersed in an aqueous solution or suspension of the immunizing antigen as an oil-in-water emulsion.

Problems were observed when using an AMPHIGEN™ adjuvant according to U.S. Pat. No. 5,084,269, above. For example, the lecithin in the AMPHIGEN™ does not suffice to produce a stable emulsion of the oil, thus leading to a pool or depot of oil in the injected tissues. Mineral oil can not be metabolized or removed by the animal. As a result, the oil becomes a source of severe chronic inflammation and scarring. Emulsifying the AMPHIGEN™ directly in the antigenic preparation carries the risk of damaging the antigen. Also, if the desired emulsion fails to form, the valuable antigen must be discarded.

An adjuvant useful in vaccines for animals, including humans, that is effective and solves the above problems would therefore be highly desirable.

SUMMARY OF THE INVENTION

The invention relates to an adjuvant useful for the enhancement of the immune response of an animal to an antigen. In particular, the invention relates to an adjuvant that is capable of forming an oil-in-water emulsion in a vaccine composition. The invention also relates to an adjuvant that, when used in a vaccine formulation, causes minimal inflammation and scarring at the vaccination site. The invention further relates to a vaccine formulation that contains an adjuvant of the invention. Finally, the invention relates to a method of using an adjuvant of the invention in a vaccination.

In one embodiment, the adjuvant of the invention comprises a lecithin, an oil and an amphiphilic surfactant capable of emulsifying the adjuvant, for example, a Tween or a Span surfactant. In another preferred aspect, the surfactant is Tween 80, Tween 85, Span 80 or Span 85.

In another embodiment, the adjuvant of the invention comprises a lecithin, an oil and two amphiphilic surfactants capable of emulsifying the adjuvant or a vaccine composition that contains the adjuvant. In a preferred aspect, one of the two surfactants is predominantly found in the aqueous phase, for example, Tween 80, and the other surfactant is predominantly found in the oil phase, for example, Span 80.

A lecithin is a phosphatide. Crude preparations of lecithin may include triglycerides. For purposes of the present invention, "lecithin" encompasses both purified and crude preparations. In a preferred aspect, the lecithin is de-oiled.

Suitable oils include a mineral oil, for example, DRAKEOL™ light mineral oil.

In a further embodiment, the adjuvant of the invention contains an aqueous carrier solution, for example, a physiologically acceptable buffer, water or a saline solution.

In a preferred embodiment, the adjuvant of the invention contains a lecithin, a mineral oil, two amphiphilic surfactants and an aqueous carrier solution (e.g., saline).

In another embodiment of the invention, a method to inactivate a culture of *Bordetella bronchiseptica* ("*B. bronchiseptica*") using formalin and glutaraldehyde is described. In another aspect, a culture of *B. bronchiseptica* is provided that was inactivated using formalin and glutaraldehyde. In yet another aspect, an antigen composition from a *B. bronchiseptica* culture is provided that was inactivated using formalin and glutaraldehyde. In yet another aspect, a vaccine composition is provided that contains an antigen composition from a *B. bronchiseptica* culture that was inactivated using formalin and glutaraldehyde.

BRIEF DESCRIPTION OF THE DRAWINGS

FIG. 1 presents a graph depicting the distribution of droplet sizes of an emulsion prepared as described below. Liries (a) and (b) depict that about 94% of the droplets have a diameter of 1 μm or less.

DETAILED DESCRIPTION OF THE INVENTION

The invention relates to an adjuvant useful for the enhancement of the immune response to an antigen. In particular, the invention relates to an oily adjuvant that is capable of emulsifying a vaccine formulation. Further, the invention relates to an adjuvant that, when used in a vaccine formulation, is capable of substantially avoiding the inflammation or scarring at the injection site, typical of vaccines containing mineral oil. Adjuvants of the invention comprise a lecithin, an oil and an amphiphilic surfactant capable of emulsifying the adjuvant or a vaccine composition that contains the adjuvant.

The invention is based, in part, on the discovery that adding from about 1.5% v/v (i.e., 1.5% volume per volume concentration obtained by, e.g., mixing 98.5 volumes of the vaccine comprising the adjuvant with 1.5 volumes of the amphiphilic surfactant) to 3.5% v/v of an amphiphilic surfactant to a vaccine containing an adjuvant as described in U.S. Pat. No. 5,084,269 is effective to sufficiently emulsify a vaccine composition formulated with such an adjuvant and to minimize irritation in the injection site of the vaccinated animal.

In one embodiment, the adjuvant of the invention contains a lecithin and an oil and an amphiphilic surfactant. In one embodiment, the adjuvant of the invention contains a lecithin and an oil and an amphiphilic surfactant capable of emulsifying a vaccine composition formulated with an adjuvant of the invention. In another preferred embodiment, two amphiphilic surfactants are used in an adjuvant of the invention, for example a Tween and a Span surfactant.

A preferred adjuvant, herein referred to as "No. 1 Adjuvant", comprises about 2% v/v lecithin, about 18% v/v mineral oil, and about 8% v/v surfactant (e.g., about 5.6% v/v Tween 80 and about 2.4% v/v Span 80), with the remaining volume being a saline solution. In a preferred aspect, a vaccine composition is formulated comprising an antigen at a concentration of about 75% v/v and an adjuvant, preferably No. 1 Adjuvant, at a concentration of about 25% v/v of the vaccine composition. All concentrations provided herein in percentage are indicated in volume per volume unless the context indicates otherwise.

Surfactants Useful in the Adjuvant of the Invention

Surfactants useful for the adjuvant of the invention are amphiphilic and acceptable for veterinary or medical use. Whether or not a particular surfactant is acceptable for medical or veterinary use can be determined by those of ordinary skill in the art. A surfactant is amphiphilic if a part of the surfactant molecule is hydrophobic and a part is hydrophilic. See U.S. Pat. Nos. 5,690,942; 5,376,369; 4,933, 179 and 4,606,918, which describe surfactants than can be used in the adjuvant of the invention. Examples of surfactants useful in the adjuvant of the invention include, but are not limited to, a Tween surfactant and a Span surfactant. Tween and Span surfactants include, but are not limited to, monolaureate (Tween 20, Tween 21, Span 20), monopalmitate (Tween 40, Span 40), monostearate (Tween 60, Tween 61, Span 60), tristearate (Tween 65, Span 65), monooleate (Tween 80, Tween 81, Span 80) and trioleate (Tween 85, Span 85). In a preferred embodiment, Tween 80, Tween 85, Span 80 or Span 85 is used.

It is preferred that a surfactant useful in the adjuvant of the invention is amphiphilic and has a hydrophilic-lipophilic balance ("HLB") value that is preferably at least about half the sum of the HLB values of all other components of the adjuvant. More preferably, the surfactant has an HLB value that is from about half to about twice the sum of the HLB values of all other components of the adjuvant. More preferably, the surfactant has an HLB value that is about the same as the HLB value of all other components of the adjuvant. HLB values are readily available for surfactants, lecithins, oils and carrier solutions or, if necessary, can be determined through routine experimentation. For example, see U.S. Pat. Nos. 4,504,275 and 4,261,925 and references provided therein.

Amphiphilic surfactants useful in the adjuvant of the invention have HLB values from about 2 to about 20, preferably from about 3 to about 17. Methods for determinig the HLB value of particular surfactants are known in the art. See for example U.S. Pat. Nos. 5,603,951; 4,933,179 and 4,606,918, which describe surfactants having particular HLB values.

The concentration of a surfactant in a vaccine composition formulated with the adjuvant of the invention is from about 1.5% to 3.5% v/v, more preferably from about 1.5% to about 3% v/v, more preferably from about 1.5% to about 2.5%, and most preferably about 2% v/v. When more than one surfactant is used, the sum of the concentrations of all surfactants used in a vaccine composition formulated with the adjuvant of the invention is also from about 1.5% to 3.5%, more preferably from about 1.5% to about 3%, more preferably from about 1.5% to about 2.5%, and most preferably about 2% v/v.

The concentration of a surfactant in the adjuvant of the invention also depends on the concentration at which the adjuvant is used in a vaccine composition. For example, a vaccine composition may be formulated with the adjuvant of the invention so that about 25% of the volume of the vaccine composition is the adjuvant ("25% adjuvant") and the remaining about 75% is made up of other components, for example the antigen composition. In one aspect, the concentration of the surfactant in a 25% adjuvant is from about 6% to 14% v/v. More preferably, the surfactant concentration in a 25% adjuvant is from about 6% to about 12%, more preferably from about 6% to about 10%, and most preferably about 8% v/v.

The concentration of the surfactant in the adjuvant of the invention is dependent on different factors. For example, the higher the concentration of oil in the adjuvant the more surfactant is required to emulsify a vaccine composition formulated with the adjuvant of the invention. Another factor that is useful to determine the concentration of a surfactant is the concentration of a lecithin. The higher the concentration of a lecithin in the adjuvant, the less surfactant may be required for emulsification.

When the adjuvant of the invention is used in a vaccine composition at a concentration of less than 25% v/v, the concentration of the adjuvant components in the adjuvant has to be increased accordingly. The aqueous carrier is an exception as the carrier always comprises the volume that remains unoccupied by all other components; thus if the concentration of all components except the carrier increases, the concentration of the carrier in the adjuvant will decrease and vice versa. For example, when the adjuvant is used at a concentration of about 12.5% v/v in a vaccine composition, the concentration of the components in the adjuvant is about twice the concentration of the components in a 25% adjuvant. Similarly, when the adjuvant of the invention is used in a vaccine composition at a concentration that is above 25% v/v, the concentration of the components in the adjuvant has to be decreased accordingly, for example when the adjuvant is used at a concentration of about 50% v/v in a vaccine composition, the concentration of the components in the adjuvant is about half the concentration of the components in a 25% adjuvant.

In one embodiment, two amphiphilic surfactants may be used in the adjuvant of the invention. Preferably, the two surfactants would include one surfactant that would be more concentrated in an aqueous phase than in an oil phase of the adjuvant ("hydrophilic surfactant") and one surfactant that would be more concentrated in an oil phase of the adjuvant ("lipophilic surfactant"). For example, Tween 80 would concentrate more in an aqueous phase and Span 80 would concentrate more in an oil phase. A preferred hydrophilic surfactant has an HLB value from about 9 to about 20 and a preferred lipophilic surfactant has an HLB value from about 2 to about 9. See U.S. Pat. Nos. 5,603,951; 4,933,179 and 4,606,918, which describe surfactants with HLB values in both ranges useful for the adjuvant of the invention.

When two surfactants are used in the adjuvant of the invention, the total concentration of both surfactants combined in a vaccine composition formulated with the adjuvant of the invention is from about 1.5% to 3.5%, more preferably from about 1.5% to about 3%, more preferably from about 1.5% to about 2.5%, and most preferably about 2% v/v. The concentration of each of two surfactants used in the adjuvant of the invention may differ from each other. For example, when a hydrophilic surfactant and a lipophilic surfactant are used, for example Tween 80 and Span 80, the concentration of Tween 80 may be from about 1.2× to about 5×, more preferably from about 1.5× to about 4×, more preferably from about 1.8× to about 3×, more preferably from about 2× to about 2.5× and more preferably about 2.3× as high as the concentration of Span 80, preferably when used in an adjuvant with a lecithin and an oil concentration as in No. 1 Adjuvant.

The concentration of the hydrophilic surfactant used in the adjuvant of the invention depends, in part, on the size of the aqueous phase, and the concentration of the lipophilic surfactant depends, in part, on the size of the oil phase. In one embodiment, the adjuvant of the invention that consists of an aqueous phase at 80% v/v and of an oil phase at 20% v/v, may contain a hydrophilic surfactant at a concentration of up to about 4 times (i.e., 80/20) the concentration of a lipophilic surfactant, or for example up to about 2 times.

Non-Surfactant Components of the Adjuvant of the Invention

In addition to an amphiphilic surfactant, the adjuvant of the invention contains a lecithin and an oil. In another aspect, the adjuvant of the invention contains an aqueous carrier solution.

Any lecithin known in the art is useful for the adjuvant of the invention. Lecithin refers to a mixture of phosphatides. When provided as a crude extract, a lecithin may also contain triglycerides. Lecithins may be of plant or animal origin. In addition, lecithins may be synthetically derived. Examples of lecithins are described in U.S. Pat. Nos. 5,690, 942; 5,597,602 and 5,084,269. In a preferred embodiment, the contents of triglycerides in a lecithin used in the adjuvant of the invention is lowered compared to its natural source, i.e., the lecithin is de-oiled. A number of ways are known in the art to de-oil a lecithin, for example as described in U.S. Pat. No. 5,597,602.

The concentration of a lecithin in a vaccine composition formulated with the adjuvant of the invention is from about 0.25% to about 12.5% v/v, more preferably from about 0.5% to about 10% v/v, more preferably from about 0.5% to about 7.5%, more preferably from about 0.5% to about 5%, more preferably from about 0.5% to about 2.5%, and most preferably from about 0.5% to about 1.25% v/v.

The concentration of a lecithin in a 25% adjuvant is at least about 1% v/v, preferably at least about 2% v/v. In another aspect, the lecithin concentration in a 25% adjuvant is from about 1% to about 50% v/v, more preferably from about 2% to about 40% v/v, more preferably from about 2% to about 30% v/v, more preferably from about 2% to about 20% v/v, more preferably from about 2% to about 10% v/v and most preferably from about 2% to about 5% v/v. The concentration of a lecithin in the adjuvant of the invention with a higher or lower concentration is determined as exemplified above.

The adjuvant of the invention contains an oil, for example an oil described in U.S. Pat. Nos. 5,814,321; 5,084,269. In a preferred aspect, the adjuvant of the invention contains a mineral oil, for example DRAKEOL™. In another aspect, a mixture of oils is used. The oil may be provided for preparation of the adjuvant of the invention as pure oil or as a mixture that contains the oil and another component, for example the lecithin.

The concentration of an oil in a vaccine composition formulated with the adjuvant of the invention is from about 1% to about 23% v/v, more preferably from about 1.5% to about 20% v/v, more preferably from about 2.5% to about 15%, more preferably from about 3.5% to about 10%, more preferably from about 3.5% to about 7.5%, more preferably from about 4% to about 6% v/v, and most preferably about 4.5%.

The concentration of an oil in a 25% adjuvant is at least about 5% v/v, preferably at least about 8% v/v and more preferably at least about 12% v/v. In another aspect, the oil concentration in a 25% adjuvant is from about 4% to about 92% v/v, more preferably from about 6% to about 80% v/v, more preferably from about 10% to about 60% v/v, more preferably from about 14% to about 40% v/v, more preferably from about 14% to about 30% v/v, more preferably from about 16% to about 24% and most preferably about 18%. The concentration of an oil in the adjuvant of the invention with a higher or lower concentration is determined as exemplified above.

In another embodiment, an aqueous carrier is used in the adjuvant of the invention, for example saline (e.g., phosphate-buffered saline), tris-HCl, citrate-phosphate buffer, Hepes buffers, other pharmaceutically acceptable buffers known in the art or water. The pH of the carrier preferably is physiologically acceptable, for example between 6 and 8, most preferably around 7. The aqueous carrier used in the adjuvant of the invention preferably takes up the volume that is not needed for any of the other components.

The adjuvant of the invention is preferably provided at a concentration that is from about 2× to about 10× the concentration after formulation of the adjuvant in a vaccine composition, more preferably from about 2× to about 8×, more preferably from about 3× to about 6× and most preferably about 4×.

Uses of Adjuvants of the Invention

Adjuvants of the invention may be used to enhance the immune response to an antigen of a vaccine formulation. Adjuvants of the invention can be used with antigens derived from any bacteria or from any virus, provided the antigen does not get destroyed or denatured. Examples of antigens, and not by way of limitation, are *Erysipelothrix rhusiopathiae* antigens, *Bordetella bronchiseptica* antigens, antigens of toxigenic strains of *Pasteurella multocida*, antigens of *Eschericia coli* strains that cause neonatal diarrhea, *Actinobacillus pleuropneumoniae* antigens, *Pasteurella haemolytica* antigens, or any combination of the above. Adjuvants of the invention are also useful in vaccine compositions that contain an antigen described in U.S. Pat. Nos. 5,616,328 and 5,084,269.

In a preferred embodiment, the adjuvant of the invention is used in a vaccine formulation containing an antigen obtained from the liquid phase of an *Erysipelothrix rhusiopathiae* ("*E. rhusiopathiae*") culture. In a preferred aspect, a culture of *E. rhusiopathiae* is inactivated by adding formalin (about 0.5% v/v final concentration) and, after incubation for 24 hours at 37° C., the cells were removed, for example by centrifugation or filtration. The culture supernatant, in a preferred embodiment, is concentrated about 10 told and aluminum hydroxide gel (preferably REHYDRAGEL™) is added to the concentrated supernatant at a final concentration of about 30% v/v to stabilize the antigen. In another preferred embodiment, thimerosal (about 0.01% v/v final concentration) (Dimportex, Spain, imported through Flavine Inc., Klosters, N.J.) with EDTA (about 0.07% v/v final concentration) are added to the antigens as preservatives. In another preferred embodiment, a vaccine composition is formulated comprising the antigen and the adjuvant of the invention (e.g. No. 1 Adjuvant) with the adjuvant comprising, for example, about 25% v/v of the vaccine composition. This preferred *E. rhusiopathiae* antigen is described in U.S. patent application Ser. No. 60/117,704, filed Jan. 29, 1999, entitled "*Erysipelothrix rhusiopathiae* Antigens and Vaccine Compositions", which is incorporated herein by reference.

In another preferred embodiment, the adjuvant of the invention is used in a vaccine composition containing antigens from a *B. bronchiseptica* culture that has been inactivated by adding formalin thereto in log phase, preferably late log phase, followed by the addition of glutaraldehyde. In addition to killing the bacterial cells, the purpose of this novel and unique inactivation is to make nontoxic the endotoxin and exotoxin *B. bronchiseptica*, while leaving the antigens of *B. bronchiseptica* cells effective in eliciting the desired immune response. Formalin is added to a concentration in the *B. bronchiseptica* culture of from about 0.2% v/v to about 1% v/v, more preferably from about 0.4% v/v to about 0.8% v/v and most preferably about 0.6% V/v. Glutaraldehyde is added from about 10 minutes to about 40 minutes following the addition of formalin to the culture, more preferably from about 15 minutes to about 30 minutes and most preferably about 20 minutes. Glutaraldehyde is added to a concentration in the *B. bronchiseptica* culture of from about 0.2% v/v to about 1% v/v, more preferably from about 0.4% v/v to about 0.8% v/v and most preferably about 0.6% v/v. Prior to adding the glutaraldehyde to the culture, it has a concentration of from about 10% v/v to about 50% v/v, more preferably from about 15% v/v to about 35% v/v and most preferably about 25% v/v. Following the addition of formalin and glutaraldehyde to the *B. bronchiseptica* culture, the resulting mix is incubated under stirring at from about 32° C. to about 42° C., more preferably at from about 35° C. to about 39° C. and most preferably at about 37° C. The mix is incubated from about 12 hours to about 60 hours, more preferably from about 24 hours to about 48 hours. All other processing steps in preparing an antigen composition of the invention from *B. bronchiseptica* culture are described in Example 7, infra, and in U.S. Pat. Nos. 5,019,388 and 4,888,169.

Vaccine Compositions Comprising Adjuvants of the Invention and their Administration The adjuvant of the invention may be used in a vaccine formulation to immunize an animal. In one embodiment, the vaccine formulation contains the adjuvant of the invention and an antigen. The optimal ratios of each component in the vaccine formulation may be determined by techniques well known to those skilled in the art.

A vaccine formulation may be administered to a subject per se or in the form of a pharmaceutical or therapeutic composition. Pharmaceutical compositions comprising the adjuvant of the invention and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen. For purposes of this application, "physiologically acceptable carrier" encompasses carriers that are acceptable for human or animal use without relatively harmful side effects (relative to the condition being treated), as well as diluents, excipients or auxiliaries that are likewise acceptable.

Systemic formulations include those designed for administration by injection, e.g. subcutaneous, intradermal, intramuscular or intraperitoneal injection.

For injection, the vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine formulation for administration is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1–36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the patient, but will typically range from about 0.1 mL to about 5 mL.

The invention having been described, the following examples are offered by way of illustration and not limitation.

EXAMPLE 1

The Use of an Adjuvant that Contains Oil and Lecithin

The following example describes the use of an adjuvant that contains de-oiled lecithin dissolved in an oil ("oil-lecithin adjuvant"), usually mineral oil (light liquid paraffin) in veterinary vaccines. See U.S. Pat. No. 5,084,269, which describes an oil-lecithin adjuvant. A vaccine preparation using an oil-lecithin adjuvant is an oil-in-water emulsion.

All percentage concentrations herein are provided in volume per volume unless indicated otherwise. Percentage values, unless otherwise indicated, of an oil-lecithin adjuvant refer to the concentration of a mixture of lecithin (10% of the mixture) and a carrier oil (DRAKEOL™) (90% of the mixture) in an aqueous carrier (continuous phase). For example, a 20% oil-lecithin adjuvant contains 2% v/v lecithin (Central Soya, Fort Wayne, Ind.), 18% v/v DRAKEOL™. 5 (Penreco, Karns City, Pa.) and 80% v/v saline solution (with the saline content being reduced if other components, for example surfactants, are added). The percentage values of an oil-lecithin adjuvant in a vaccine composition, i.e., following dilution of the adjuvant solution with the antigen solution, refer to the concentration of a mixture of lecithin (10% of mixture) and a carrier oil (DRAKEOL™) (90% of mixture) in the vaccine preparation which comprises the adjuvant and a solution containing an antigen, unless the context indicates otherwise. In all cases where a surfactant was added to an adjuvant composition, the percentage values for a surfactant concentration refer to the total concentration of all added surfactants in the adjuvant or the vaccine preparation, unless the context indicates otherwise.

When an oil-lecithin adjuvant was used as an adjuvant in vaccine formulations, it was found that it does not emulsify aqueous preparations without the addition of extra surfactants as the lecithin in the oil-lecithin adjuvant did not suffice for emulsification. Therefore, vaccines made using inadequately dispersed oil-lecithin adjuvant formed a pool or depot of mostly mineral oil in the tissues at the injection site. This oil can not be metabolized or removed by the injected animal and so it remains as a source of severe chronic inflammation and scarring.

It was also determined that adding surfactants to a vaccine formulation comprising an oil-lecithin adjuvant and an antigen in order to emulsify the formulation was not an adequate solution. Problems encountered when adding oil and surfactants to the vaccine formulation before emulsifying were that the antigen could get damaged and, if a suitable emulsion was not achieved, that the formulation would have to be discarded including the valuable antigen.

Different adjuvant compositions were tested comprising an oil-lecithin adjuvant in combination with surfactants to emulsify the vaccine formulations.

EXAMPLE 2

The Use of an Adjuvant Containing a Surfactant at a Low Concentration

The following example describes the use of an emulsion containing 40% oil-lecithin and 2% of synthetic surfactants, i.e., Tween 80 and Span 80 (Van Water & Rogers, Omaha, Nebr.) in phosphate buffered saline. This adjuvant was prepared aseptically and separate from the antigen. The emulsion was added to the antigen preparation without further emulsification. The synthetic surfactants helped the oil-lecithin adjuvant to disperse as a coarse, relatively stable emulsion. The adjuvant emulsion was added to the aqueous antigenic preparation at the rate of one in eight, decreasing the oil-lecithin adjuvant content from 40% to 5%, and the surfactants from a combined 2% to 0.25%.

The adjuvant was used in several vaccines. It was found that because the emulsion is coarse and not very stable, the oil droplets tend to coalesce and to separate as a permanent, irritating depot of oil in the injected tissues. Another problem observed with this adjuvant was that it aggregates with Al gel. A number of vaccines contain Al gel for a number of purposes like, for example, as an adjuvant or to stabilize an antigen or to bind endotoxin. The oil-lecithin adjuvant carries a negative charge which causes it to bind to the positively charged Al gel to form coarse aggregates. These aggregates are unsightly, difficult to pass through a hypodermic needle, and very irritating to the injected tissues.

EXAMPLE 3

The Use of an Adjuvant Containing a Surfactant at a High Concentration

An oil-lecithin adjuvant (5% v/v) was emulsified in the antigenic preparation with the help of Tween 80 and Span 80 surfactants, as above, but at a total surfactant concentration of 8% in the vaccine composition. The emulsion was very fine and stable. It had almost the clarity of a solution and it did not cream on standing. Under the microscope, with maximum magnification (resolution 0.2 micron), most droplets were too small to be visible. Thus, it was a microemulsion. This adjuvant, when used in a vaccine formulation, was found to be virtually free of injection-site reactivity and, when Al gel was added, there was no detectable aggregation of oil and gel. As a result of its high surfactant content, this adjuvant is easy to emulsify, attractive in appearance, stable, unreactive with Al gel, and virtually free of irritating effects at the site of vaccination. Despite these advantages, however, this emulsion had slightly lower adjuvant potency compared to the coarse version made with surfactants at a low concentration.

EXAMPLE 4

The Use of an Adjuvant Containing a Surfactant at a Medium Concentration

An attempt was made to find an adjuvant emulsion that is acceptably smooth and fully potent as an adjuvant. A 20% oil-lecithin adjuvant was used in these experiments as it was found that a 20% oil-lecithin adjuvant emulsion is easier to make than a 40% oil-lecithin adjuvant emulsion. Its addition to vaccines at a rate of one in four, to make a final oil concentration of 5%, would leave 75% of the dose volume for antigens. Preliminary experiments showed that a smooth submicron emulsion (most droplets had a diameter of less than one micron, see FIG. 1) could be prepared with 20% oil and 16% of Tween 80 and Span 80 surfactants.

Two emulsions were prepared for the assays. One contained a 20% oil-lecithin adjuvant and 16% of Tween 80 and Span 80 surfactants. Diluting it one in four resulted in an emulsion comprising 5% oil-lecithin adjuvant and 4% surfactants in the vaccine preparation. The other emulsion was prepared with a 40% oil-lecithin adjuvant and 2% of Tween 80 and Span 80 surfactants. Diluting it one in eight gave an emulsion with 5% oil-lecithin adjuvant and 0.25% surfactants.

Al gel (REHYDRAGEL™ obtained from Reheis, Berkeley Heights, N.J.) was added to a concentration of 10% to samples of each emulsion. In the emulsion with 0.25% surfactants the oil and Al gel aggregated and separated to form a thick layer at the top of the liquid column (creaming).

In the emulsion with 4% surfactants, by contrast, there was no aggregation or creaming. With 4% surfactants, the Al gel sedimented at the bottom of the tube leaving the oil droplets dispersed in the supernatant fluid.

EXAMPLE 5

Swelling of Injection Sites when Using an Adjuvant Containing a Surfactant at a Medium Concentration Vaccine preparations were tested in pigs to determine whether swelling of the injection site occurred when an adjuvant with a medium concentration of surfactant was used. Vaccine preparations that contain a 5% oil-lecithin adjuvant and either 0.25% or 4% surfactants caused no swelling in pigs at the injection site. When Al gel was added to the vaccine preparation at a concentration of 10%, the preparation with 0.25% surfactants caused severe injection site swellings whereas the one with 4% surfactants resulted in almost no swelling.

Experiments were carried out to determine the range of surfactant concentrations that are effective in preventing aggregation with Al gel and swelling of the injection site. When using a 1.5% surfactant concentration in the vaccine, slight aggregation of oil and Al gel was observed. The aggregation was much heavier at lower surfactant concentrations. At 2% and 4% surfactant concentrations, there was no aggregation. The swelling induced in pigs by vaccine preparations containing 0.5% or less surfactants were larger at 2 and 4 weeks after vaccination than those induced by preparations with 1% or more surfactants. By 6 weeks after vaccination, it was evident that 1.5% surfactants was the minimum needed to avoid chronic swellings.

EXAMPLE 6

Adjuvants with Useful In Vitro and In Vivo Properties

Assays were carried out to find an adjuvant that does not react with Al gel and does not lead to reactivity in the animal following vaccination. A 20% oil-lecithin adjuvant that contains 8% surfactants, resulting in a vaccination preparation with 5% oil-lecithin adjuvant and 2% surfactant, was determined to be sufficient to avoid both in vitro reactivity with Al gel and irritation of the tissues at the vaccination site. Evidence of a relationship between surfactant concentration and adjuvant power was much less clear. There were occasional indications that 4% surfactants in the vaccine was excessive, e.g. in the induction of agglutinin to *E. coli* K99, and neutralizing antitoxin to the toxin of *P. multocida* Type D.

Thus, it was determined that the optimal concentration of surfactants was 8% in a 20% oil-lecithin adjuvant, resulting in 2% surfactants in the vaccine composition. This provided for reasonably easy emulsification and for good stability in cold storage. In vaccines with 5% oil-lecithin adjuvant, 2% surfactants was ideal for both adjuvant power and freedom from irritancy in the injected tissues.

The droplet size in the submicron emulsion of a 20% oil-lecithin adjuvant with 8% surfactants was determined. The 8% surfactant consisted of 5.6% Tween 80 in the aqueous phase and 2.4% Span 80 in the oil phase. About 94% of all droplets were less than 1 micron in diameter, see FIG. 1.

A stock of 100 mL of a 20% oil-lecithin adjuvant with 8% surfactants was made from 200 mL filter-sterilized lecithin-oil solution (10% lecithin in DRAKEOL™ mineral oil), autoclaved Tween 80 (56 mL) and Span 80 (24 mL), and phosphate buffered saline (720 mL) (Dulbecco PBS). The lecithin-oil solution and Span 80 were combined and mixed in a sterile tank for at least 1 hour at room temperature until emulsification was complete. The saline and Tween 80 were combined and mixed in a sterile tank for at least 1 hour at room temperature. The oil mixture was emulsified in the aqueous mixture using an emulsifier. Emulsification was continued by recirculation until all of the adjuvant was added into the saline. The emulsion was then passed twice through a homogenizer at room temperature. The adjuvant was stored at 2 to 80 C.

EXAMPLE 7

Atrophic Rhinitis Vaccine Using an Adjuvant Containing a Surfactant at a Medium Concentration The adjuvant as described in Example 4 with a medium concentration of surfactants was used in an Atrophic Rhinitis Vaccine which contained antigens of *Bordetella bronchiseptica* and toxigenic *Pasteurella multocida*. A *Bordetella bronchiseptica-Pasteurella multocida* Bacterin-Toxoid vaccine was made from *B. bronchiseptica* cells and the toxoid of *P. multocida*.

*B. bronchiseptica* cells, strain 2-9 NADL, were prepared as described in U.S. Pat. Nos. 5,019,388 and 4,888,169 except that at the end of the growth cycle, cultures were continuously mixed and formalin solution was added to a final concentration of 0.6%. Within 20 minutes after the addition of formalin, a 25% glutaraldehyde solution was added to a final concentration of 0.6%. The culture was stirred for 24 to 48 hours at 37+2° C. to complete inactivation and detoxification. (See Table 1). Then, the culture fluids were cooled to 15° C. or less for processing. Inactivated cultures not processed immediately were stored at 2 to 8° C. for up to 14 days. Following inactivation, the bacteria were separated from the culture fluid by centrifugation. The supernatant was discarded and the cells were resuspended in phosphate-buffered saline at approximately one tenth of the original volume. The concentrated suspension was stored at 2 to 8° C. The treatment of *B. bronchiseptica* with two aldehydes inactivates both the endotoxin and the exotoxin, obviating other treatments for safety.

The toxoid of *P. multocida* was prepared in two different forms as described in U.S. Pat. Nos. 5,536,496 and 5,695, 769. In one form, the toxin is toxoided within the bacterial cells by the addition of formaldehyde to the culture; the toxoid stays inside the cells. In the other form, the live cells are mechanically disrupted and the toxin extracted. The toxin is toxoided by exposure to a high pH, as described in U.S. Pat. No. 5,536,496. Both forms of the toxoid are treated with Al gel to control free endotoxin by a patented process, as described in U.S. Pat. No. 5,616,328. (See Table 1). A synergy between the two forms of pasteurella toxoid results in antitoxin responses far exceeding the sum of the responses to each form when used alone as described in U.S. Pat. No. 5,695,769.

TABLE 1

Treatment of cells during preparation of the *Bordetella Bronchiseptica-Pasteurella Multocida* Bacterin-Toxoid vaccine

| Antigen | Inactivant | Concentration | Target Temp. Range | Time (Min/Max) |
|---|---|---|---|---|
| *B. bronchiseptica* | Formalin | 0.6% | 37 ± 2° C. | 24–48 hours |
| | Glutaraldehyde | 0.6% | | |
| *P. multocida* cell-bound toxoid | Formalin | 0.4% | 37 ± 2° C. | 5 days |
| *P. multocida* cell-free toxoid | 5N NaOH | pH 10 ± 0.2 | 15 ± 2° C. | 1 to 6 hours |

The adjuvant described in Example 4 was added to result in concentrations of 5% oil-lecithin adjuvant and 2% surfactants in the vaccine formulation.

A trial to determine the minimum immunizing dose of the atrophic rhinitis vaccine demonstrated the adjuvant properties of the oil-lecithin adjuvant with a medium concentration of surfactants. Pregnant sows were vaccinated with two 2 mL doses at an interval of 4 weeks. They farrowed about 2 weeks after the second dose. At one month of age, their pigs were subjected to a severe challenge, consisting of virulent *B. Bronchiseptica* and *P. Multocida* cultures given intranasally in sequence. The pigs born to 7 sows vaccinated only with a placebo developed severe atrophic rhinitis. The litters of all 7 sows given vaccine containing a full dose of the antigens were strongly protected by the maternal antibody still in circulation. Sows given vaccines containing ½ or ⅛ dose of antigens did not provide their litters with satisfactory protection.

EXAMPLE 8

Erysipelas Vaccine Using an Adjuvant Containing a Surfactant at a Medium Concentration The adjuvant described in Example 4 with a medium concentration of surfactants was used in an erysipelas vaccine which contained *E. rhusiopathiae* antigens. The antigens for use in a vaccine were made from *E. rhusiopathiae* cultures inactivated with 0.5% formalin for at least 24 hours. The inactivated cultures were clarified by centrifuging, and concentrated roughly tenfold by molecular filtration. The concentrates were stabilized by adding Al gel, i.e., REHYDRAGEL™, to a concentration of 30%. The preadsorbed concentrates were included in the vaccine in an amount such that each 2 mL dose contained at least 3.2 opacity units (OU) as calculated from the optical density (OD) of the culture at inactivation. (The OD is multiplied by the final concentration factor to give a value in OU per mL.)

An Erysipelas vaccination was carried out to determine the efficacy of a vaccine containing the oil-lecithin adjuvant with a medium concentration of surfactants. The adjuvant as described in Example 4 was added at a final concentration of 25% v/v, giving a final lecithin oil concentration of 5%. Thimerosal (0.01% w/v), with EDTA (0.07% w/v), was added as preservative.

Vaccines made according to this formula were tested twice for efficacy in pigs. In each case pigs were vaccinated with two 2 mL doses given intramuscularly (IM) one dose at about 3 weeks (weaning) and the second dose 3 weeks later. Controls received phosphate-buffered saline as a placebo. Immunity was challenged by the IM injection of virulent *E. Rhusiopathiae* at about 9 weeks of age in one study and 6 months of age in the other. As shown in Table 2, protection due to vaccination was 100% at 9 weeks and 75% at 6 months (i.e., slaughter age). These results indicated that the vaccine provides satisfactory protection against Erysipelas throughout the normal feeding period.

The vaccine used in the group challenged at 9 weeks was already 12 months old. The result confirms that the protective antigen was successfully stabilized.

TABLE 2

Protection of pigs against Erysipelas

| Age at Challenge | Controls (Protected/Challenged) | Vaccinates (Protected/Challenged) |
|---|---|---|
| 9 weeks | 0/10 | 19/19 |
| 6 months | 0/10 | 15/20 |

Note: In the vaccinated group challenged at 9 weeks, the 20th pig was excluded. A very fractious animal, it struggled so violently when handled that its temperature at rest could not be determined. Following challenge this pig remained completely healthy.

The invention is not to be limited in scope by the exemplified embodiments which are intended as illustrations of single aspects of the invention, and any adjuvants which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for protecting a piglet against atrophic rhinitis by:

a) providing a vaccine comprising *Bordetella bronchiseptica* cells inactivated by adding formalin followed by adding 0.4% to 0.8% volume per volume concentration ("v/v") of glutaraldehyde to the cells, toxigenic *Pasteurella multocida* antigens, and a physiologically acceptable carrier;

b) providing a female pig;

c) vaccinating the female pig prior to furrowing and during pregnancy with an amount of the vaccine effective to provide anti-*Bordetella bronchiseptica* antibodies and anti-toxigenic *Pasteurella multocida* antibodies in colostrum produced by the female pig;

d) bringing the colostrum into association with a piglet and providing the colostrum produced by the female pig to the piglet within about 24 hours subsequent to the piglet's birth.

* * * * *